(12) United States Patent
Xing et al.

(10) Patent No.: US 11,802,520 B2
(45) Date of Patent: Oct. 31, 2023

(54) METHOD AND SYSTEM FOR WATER IN FUEL PROGNOSTIC MONITOR

(71) Applicant: Ford Global Technologies, LLC, Dearborn, MI (US)

(72) Inventors: Yun Xing, Canton, MI (US); Brien Fulton, Bloomfield Hills, MI (US); Hassene Jammoussi, Canton, MI (US); John Erik Mikael Hellstrom, Ann Arbor, MI (US); Carlos Armesto, Canton, MI (US); William P. Boone, Northville, MI (US); Alex John William Michael Howard, Halstead (GB)

(73) Assignee: Ford Global Technologies, LLC, Dearborn, MI (US)

( * ) Notice: Subject to any disclaimer, the term of this patent is extended or adjusted under 35 U.S.C. 154(b) by 26 days.

(21) Appl. No.: 17/448,671

(22) Filed: Sep. 23, 2021

(65) Prior Publication Data
US 2023/0088463 A1    Mar. 23, 2023

(51) Int. Cl.
*F02D 41/30* (2006.01)
*G01N 33/28* (2006.01)
*F02D 41/22* (2006.01)

(52) U.S. Cl.
CPC ............ *F02D 41/22* (2013.01); *F02D 41/3082* (2013.01); *G01N 33/2847* (2013.01); *F02D 2041/224* (2013.01); *F02D 2041/228* (2013.01); *F02D 2200/0602* (2013.01); *F02D 2200/0611* (2013.01)

(58) Field of Classification Search
CPC .................. F02D 41/22; F02D 41/3082; F02D 2041/224; F02D 2041/228; G01N 33/2487; F02D 2200/0602; F02D 2200/0611
See application file for complete search history.

(56) References Cited

U.S. PATENT DOCUMENTS

| | | | |
|---|---|---|---|
| 6,974,537 B2 | 12/2005 | Abdelqader | |
| 8,781,673 B2* | 7/2014 | Nunn et al. | F02D 41/0025 702/50 |
| 2020/0079330 A1* | 3/2020 | Dudar | F02D 41/042 |
| 2020/0263652 A1* | 8/2020 | Kiwan et al. | F02P 5/1502 |
| 2020/0277905 A1* | 9/2020 | Agnus et al. | F02D 41/009 |
| 2022/0107303 A1* | 4/2022 | Goltzman et al. | F02M 37/28 |

FOREIGN PATENT DOCUMENTS

| | | | |
|---|---|---|---|
| DE | 102007061125 A1 | | 7/2008 |
| EP | 3017159 B1 | | 10/2017 |

* cited by examiner

*Primary Examiner* — George C Jin
(74) *Attorney, Agent, or Firm* — Vincent Mastrogiacomo; McCoy Russell LLP

(57) ABSTRACT

A method for determining the presence of water and diesel exhaust fluid mixed with diesel fuel is disclosed. In one example, output pressure of a fuel pump may be indicative of the presence or absence of water in diesel fuel. The presence or absence of water in fuel may be evaluated in response to filling a fuel tank.

20 Claims, 4 Drawing Sheets

METHOD AND SYSTEM FOR WATER IN FUEL PROGNOSTIC MONITOR

BACKGROUND/SUMMARY

A compression ignition engine may be supplied with diesel fuel via a high pressure pump, a low pressure pump, and fuel injectors. The diesel fuel may be stored in tanks where condensation within the tank results in water mixing in with the diesel fuel. In addition, water may be introduced into the diesel fuel in other ways. Water in the diesel fuel may cause reduced engine performance, high pressure fuel pump degradation, and fuel injector degradation. Therefore, it may be desirable to reduce exposing the high pressure fuel pump and fuel injectors to mixtures of fuel and water. One way to reduce a possibility of delivering water to a compression ignition engine and high pressure fuel pump may be to install a water separator along a fuel line that leads from a fuel tank to the high pressure fuel pump. The water separator may include a sensor to provide an indication that an amount of water in a reservoir of the separator is greater than a threshold amount. Depending on the ratio of water to fuel, it may take a substantial amount of time for the separator to indicate that water is mixed in the fuel and that vehicle service may be advised. Consequently, the separator may provide a useful function, but the water separator may not provide any indication that water may pass through the separator and reach the high pressure fuel pump and engine.

The inventors herein have recognized the above-mentioned disadvantages and have developed a method for operating a vehicle, comprising: activating a fuel pump and determining an amount of time for a pressure downstream of the fuel pump to reach a threshold pressure in response to an indication of a fuel tank receiving a fluid.

By activating a low pressure fuel pump and determining an amount of time it takes for pressure downstream of the low pressure fuel pump to reach a threshold pressure, it may be possible to provide the technical result of determining the presence or absence of water in fuel. The low pressure fuel pump may be placed downstream of a water separator so that the pressure downstream of the low pressure fuel pump may be indicative of water that may reach the high pressure fuel pump. As such, early notification of water in fuel may be provided to a human driver of a vehicle.

The present description may provide several advantages. For example, the approach may reduce a possibility of engine and fuel system degradation. Further, the approach may provide improved estimates of water levels of a water reservoir. In addition, the approach may detect water and diesel exhaust fluid in a fuel system.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
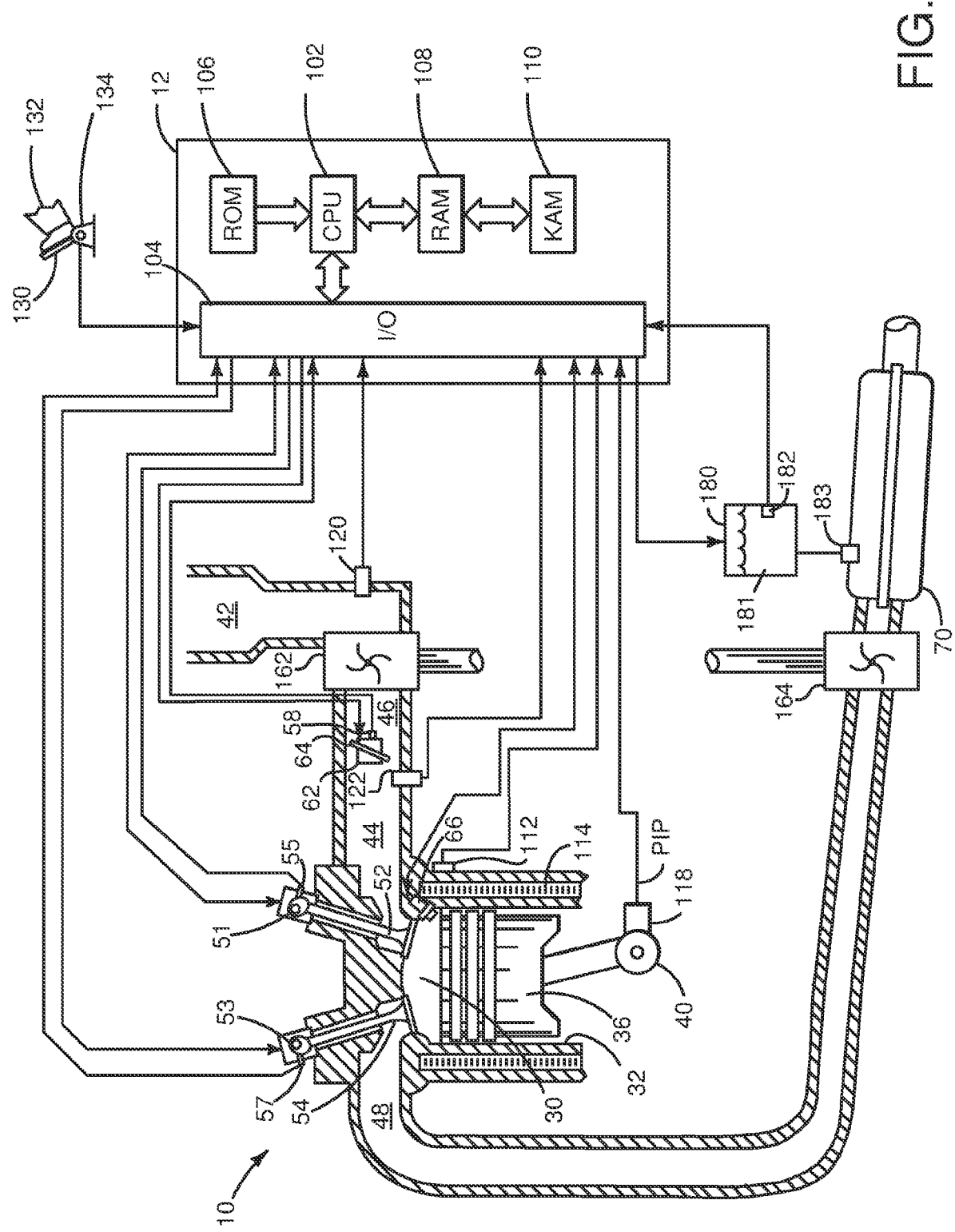
FIG. 1 shows a schematic depiction of an engine.
Figure 2:
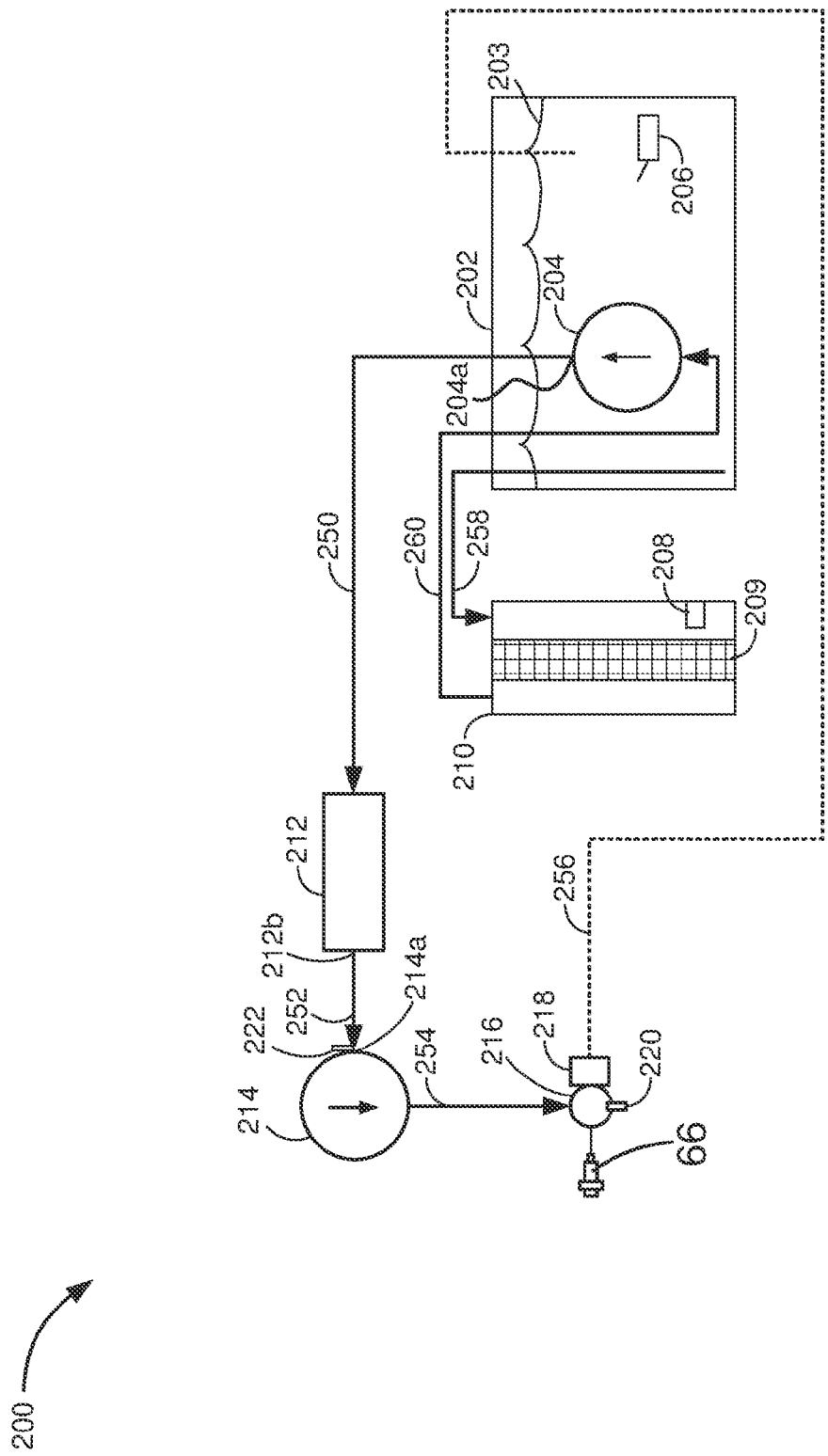
FIG. 2 shows a schematic depiction of a fuel system for the engine of FIG. 1.
Figure 3:
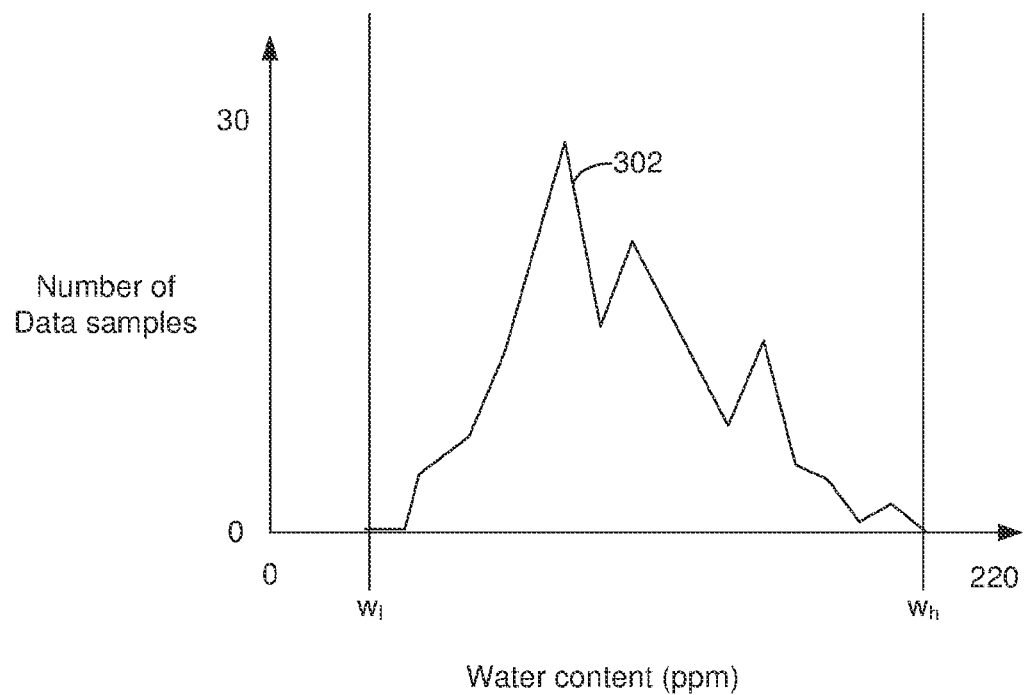
FIG. 3 is a plot of an example distribution for water content in diesel fuel.
Figure 4:
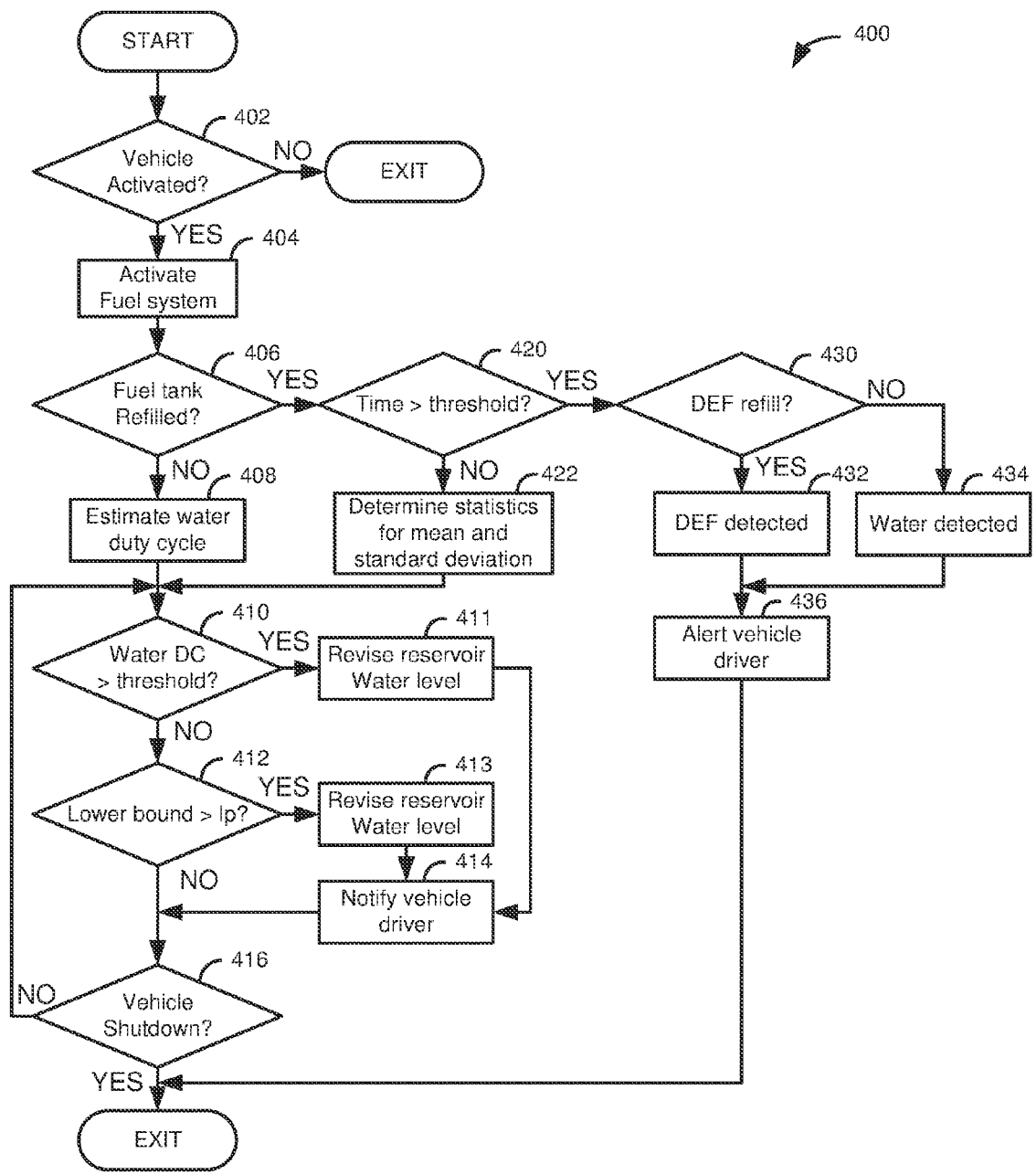
FIG. 4 shows an example method for determining water in diesel fuel.

The present description is related to implementing a water in fuel prognostic monitor for a diesel vehicle. FIG. 1 shows one example of a boosted direct injection compression ignition engine where the method of FIG. 4 may be implemented to indicate water in fuel. FIG. 2 shows an example fuel system for the engine of FIG. 1. FIG. 3 shows an example distribution of water in diesel fuel. FIG. 4 shows a flow chart of a method for determining the presence of water in diesel fuel.

Referring to FIG. 1, internal combustion engine 10, comprising a plurality of cylinders, one cylinder of which is shown in FIG. 1, is controlled by electronic engine controller 12. Engine 10 includes combustion chamber 30 and cylinder walls 32 with piston 36 positioned therein and connected to crankshaft 40. Combustion chamber 30 is shown communicating with intake manifold 44 and exhaust manifold 48 via respective intake valve 52 and exhaust valve 54. Each intake and exhaust valve may be operated by an intake cam 51 and an exhaust cam 53. The position of intake cam 51 may be determined by intake cam sensor 55. The position of exhaust cam 53 may be determined by exhaust cam sensor 57.

Fuel injector 66 is shown positioned to inject fuel directly into cylinder 30, which is known to those skilled in the art as direct injection. Fuel injector 66 delivers liquid fuel in proportion to the pulse width of a signal from controller 12. Fuel is delivered to fuel injector 66 by a fuel system (not shown) including a fuel tank, fuel pump, fuel rail (not shown). Fuel pressure delivered by the fuel system may be adjusted by varying a position valve regulating flow to a fuel pump (not shown). In addition, a metering valve may be located in or near the fuel rail for closed loop fuel control.

Intake manifold 44 is shown communicating with optional electronic throttle 62 which adjusts a position of throttle plate 64 to control air flow from intake boost chamber 46. Compressor 162 draws air from air intake 42 to supply boost chamber 46. Exhaust gases spin turbine 164 which is coupled to compressor 162.

Combustion is initiated in combustion chamber 30 when fuel automatically ignites as piston approaches top-dead-center compression stroke. In some examples, a universal Exhaust Gas Oxygen (UEGO) sensor (not shown) may be coupled to exhaust manifold 48 upstream of emissions device 70. In other examples, the UEGO sensor may be located downstream of one or more exhaust after treatment devices. Further, in some examples, the UEGO sensor may be replaced by a NOx sensor.

Emissions device 70 can include a particulate filter and catalyst bricks, in one example. In another example, multiple emission control devices, each with multiple bricks, can be used. Emissions device 70 can include an oxidation catalyst in one example. In other examples, the emissions device may include a lean NOx trap or a SCR.

Diesel exhaust fluid (DEF) 181 may be comprised of water and urea. DEF may be stored in reservoir 180 that includes a level sensor 182. The DEF may be injected to the emissions device 70 via injector 183 to reduce NOx into nitrogen and water. DEF may be refilled via a tube or pipe that may be located near the diesel fuel fill tube.

Controller 12 is shown in FIG. 1 as a conventional microcomputer including: microprocessor unit 102, input/output ports 104, read-only memory (e.g., non-transitory memory) 106, random access memory 108, keep alive memory 110, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a position sensor 134 coupled to an accelerator pedal 130 for sensing accelerator position adjusted by foot 132; a measurement of engine manifold pressure (MAP) from pressure sensor 122 coupled to intake manifold 44; an engine position sensor from a Hall effect sensor 118 sensing crankshaft 40 position; a measurement of air mass entering the engine from sensor 120 (e.g., a hot wire air flow meter); and a measurement of throttle position from sensor 58. Barometric pressure may also be sensed (sensor not shown) for processing by controller 12. In a preferred aspect of the present description, engine position sensor 118 produces a predetermined number of equally spaced pulses every revolution of the crankshaft from which engine speed (RPM) can be determined.

In some embodiments, the engine may be coupled to an electric motor/battery system in a hybrid vehicle. The hybrid vehicle may have a parallel configuration, series configuration, or variation or combinations thereof.

During operation, each cylinder within engine 10 typically undergoes a four stroke cycle: the cycle includes the intake stroke, compression stroke, expansion stroke, and exhaust stroke. During the intake stroke, generally, the exhaust valve 54 closes and intake valve 52 opens. Air is introduced into combustion chamber 30 via intake manifold 44, and piston 36 moves to the bottom of the cylinder so as to increase the volume within combustion chamber 30. The position at which piston 36 is near the bottom of the cylinder and at the end of its stroke (e.g. when combustion chamber 30 is at its largest volume) is typically referred to by those of skill in the art as bottom dead center (BDC). During the compression stroke, intake valve 52 and exhaust valve 54 are closed. Piston 36 moves toward the cylinder head so as to compress the air within combustion chamber 30. The point at which piston 36 is at the end of its stroke and closest to the cylinder head (e.g. when combustion chamber 30 is at its smallest volume) is typically referred to by those of skill in the art as top dead center (TDC). In a process hereinafter referred to as injection, fuel is introduced into the combustion chamber. In some examples, fuel may be injected to a cylinder a plurality of times during a single cylinder cycle. In a process hereinafter referred to as ignition, the injected fuel is ignited by compression ignition or by known ignition means such as spark plug (not shown), resulting in combustion. During the expansion stroke, the expanding gases push piston 36 back to BDC. Crankshaft 40 converts piston movement into a rotational torque of the rotary shaft. Finally, during the exhaust stroke, the exhaust valve 54 opens to release the combusted air-fuel mixture to exhaust manifold 48 and the piston returns to TDC. Note that the above is described merely as an example, and that intake and exhaust valve opening and/or closing timings may vary, such as to provide positive or negative valve overlap, late intake valve closing, or various other examples. Further, in some examples a two-stroke cycle may be used rather than a four-stroke cycle.

Referring now to FIG. 2, a detailed view of fuel system 200 for the engine of FIG. 1 is shown. Fuel system 200 includes a fuel tank 202 for storing liquid fuel 203. Fuel 203 may be drawn from fuel tank 202 via conduit or pipe 258 into water separator 210. Water separator 210 includes a water in fuel sensor 208 and a water reservoir 209. Fuel that passes through the water separator 210 may flow to a low pressure fuel pump 204 via conduit or pipe 260. Low pressure fuel pump 204 delivers fuel to a filter 212 from outlet 204a of low pressure fuel pump 204. Fuel exits filter 212 and flows to high pressure pump via conduit 252 and fuel pressure may be measured at an inlet of high pressure fuel pump 214a via pressure sensor 222. Alternatively, pressure sensor 222 may be positioned anywhere along conduit 250 or conduit 252, including at outlet 204a of low pressure fuel pump 204 or at the outlet 212b of fuel filter 212. High pressure fuel pump 214 delivers fuel to fuel rail 216 via conduit 254. Fuel rail 216 includes a pressure sensor and a regulator 218. Fuel may be delivered from fuel rail 216 to engine 10 via fuel injector 66. Regulator 218 may return fuel to fuel tank 202 via conduit or pipe 256 when fuel pressure exceeds a threshold level. A level of fuel in fuel tank 202 may be provided by fuel level sensor 206. The arrows along conduits 258, 260, 250, 252, and 254 indicate the direction of fuel flow from fuel tank 202 to low pressure fuel pump 204 and to high pressure fuel pump 214. Thus, high pressure fuel pump 214 is positioned downstream of low pressure fuel pump 204 according to the direction of fuel flow.

Thus, the system of FIGS. 1 and 2 provides for a vehicle system, comprising: an internal combustion engine; a first fuel pump and a second fuel pump supplying fuel to the internal combustion engine; a fuel tank; and a controller including executable instructions stored in non-transitory memory to activate the first fuel pump and determine an amount of time for a pressure downstream of the first fuel pump to reach a threshold pressure in response to an indication of a fluid being added to the fuel tank. The vehicle system further comprises additional instructions to estimate an amount of water in a water reservoir in response to the amount of time being less than a threshold amount of time. The vehicle system further comprises additional instructions to indicate water in a fuel when the amount of time exceeds a threshold amount of time. The vehicle system further comprises additional instructions to indicate diesel exhaust fluid in a fuel when the amount of time exceeds a threshold amount of time. The vehicle system further comprises additional instructions to determine a duty cycle of water stored in a water reservoir. The vehicle system further comprises additional instructions to estimate a diesel fuel water content. The vehicle system further comprises additional instructions to estimate a distance a vehicle may travel before an amount of water stored in a water reservoir reaches a diagnostic level. The vehicle system further comprises additional instructions to adjust a reservoir water level based on a diesel fuel water content.

Turning now to FIG. 3, a plot of an example distribution of water in diesel fuel is shown. Plot 300 includes a vertical axis that represents an actual number of data samples taken for water in fuel. The actual total number of data samples taken for water in fuel increases in the direction from the horizontal axis to the vertical axis arrow. The horizontal axis represents water content in fuel and the water content in the fuel increases in the direction of the horizontal axis arrow. Curve 302 represents water content in fuel. The lower boundary of water in fuel is indicated by the vertical line $w_1$ and the upper boundary of water in fuel is indicated by the vertical line $w_h$. It may be observed that curve 302 exhibits a shape that is similar to a normal distribution.

Referring now to FIG. 4, a flowchart of an example method for detecting water in diesel fuel is shown. The method of FIG. 4 may be incorporated into and may cooperate with the system of FIGS. 1-2. Further, at least portions of the method of FIG. 4 may be incorporated as executable instructions stored in non-transitory memory while other portions of the method may be performed via a controller transforming operating states of devices and actuators in the physical world.

At 402, method 400 determines if the vehicle that includes the engine and fuel system of FIG. 1 is activated. Method 400 may determine that the vehicle is activated based on a position of a key switch, a push button input, a proximity of a key fob, a state of a variable in controller memory, or other known way of activating a vehicle. If method 400 judges that the vehicle is activated, the answer is yes and method 400 proceeds to 404. Otherwise, the answer is no and method 400 proceeds to exit.

At 404, method 400 activates the vehicle's fuel system. Activating the vehicle's fuel system may include activating and/or providing power to one or more fuel pumps in the fuel system. Method 400 may also open and/or close valves to active the vehicle's fuel system. Method 400 proceeds to 406.

At 406, method 400 judges whether or not a fluid has been added to the vehicle's fuel tank. The fluid is preferably fuel, but it may be possible to add other fluids to the fuel tank. If so, the answer is yes and method 400 proceeds to 420. Otherwise, the answer is no and method 400 proceeds to 408. In one example, method 400 may determine if the fuel tank has been refilled according to the following equation:

$$h_n > h_0 + \varepsilon \qquad (1)$$

where $h_n$ is the present level output via a fuel level sensor, $h_0$ is a saved fuel level from a most recent time that the vehicle was deactivated, and $\varepsilon$ is a threshold offset value.

At 408, method 400 estimates a water duty cycle value. In one example, method 400 estimates the water duty cycle value as described in U.S. Pat. No. 8,781,673, which is hereby fully incorporated for all intents and purposes. For example, the duty cycle may be determined via the following equation:

$$DutyCycle = \frac{water\ sum(1) + water\ sum(2) + water\ sum(y)}{bin\ size(n) \cdot num\ bins(y)} \qquad (2)$$

where Duty Cycle is the duty cycle value, water sum (1) is a sum of outputs of a water in fuel sensor for a first bin (e.g., group of memory locations) of water in fuel samples that includes n samples, water sum (2) is a sum of outputs of the water in fuel sensor for a second bin of water in fuel samples that includes n samples, bin size (n) is the total number of water in fuel sensor samples in each bin, and num bins (y) is the total number of bins y. For example, when an output data sample measurement received from the water in fuel sensor indicates that prongs of the second are submerged in water, the cumulative data sum for a bin may increase by a value of one. After a nth water in fuel data output sample is collected, the cumulative sum may be stored in the water sum variable for a particular bin and the bin count number may be increased. A next working data bin may then receive n output samples from the water in fuel sensor. A second stored water sum may then be stored and the bin counter may be increased by one. The collecting and processing of water in fuel sensor output data may be repeated until the bin counter reaches a predetermined value y. All stored water sum values up to sum y may be tallied as part of equation 1. The duty cycle calculation represents a percentage of data sample water in fuel measurements that indicate that the prongs of the water in fuel sensor are submerged in water. One of the bins of data may be replaced with newer output data from the water in fuel sensor after each time the duty cycle is determined. Method 400 proceeds to 410.

At 410, method 400 judges if the water duty cycle value determined at 408 is greater than a threshold. If so, the answer is yes and method 400 proceeds to 411. Otherwise, the answer is no and method 400 proceeds to 412.

At 411, method 400 revises the reservoir water level (e.g., an amount of water in the water reservoir of the fuel separator (e.g., 210 of FIG. 2). In particular, the amount of water in the reservoir (water$_{reservoir}$) may be adjusted to equal the minimum detectable level of water in fuel ($l_p$) that is detectable by the water in fuel sensor. The value of lp may be a function of geometry of the water in fuel sensor. Method 400 also updates the value of the diesel fuel water content according to the following equation:

$$\delta = \frac{l_p}{total\ fuel\ filled} \qquad (3)$$

where $\delta$ is the diesel fuel water content, $l_p$ is the amount of water that is in the water reservoir, and total fuel filled in the fuel tank is given via the following equation:

$$total\ fuel\ filled = \sum_i \{f(h_n - h_0)\} \qquad (4)$$

where total fuel filled is the amount of fuel that is added to the fuel tank during a series of refills, f is a function that returns a fuel amount based on the present fuel level $h_n$ and the fuel level before the most recent refill $h_0$.

Method 400 also estimates a number of miles before the water in the water reservoir reaches a diagnostic level. In particular, method 400 estimates the remaining number of miles before the water level in the water reservoir reaches a diagnostic level $l_d$ via the following equation:

$$distance\ to\ diagnostic = \frac{l_d - l_p}{\delta} \cdot MPG \qquad (5)$$

where distance to diagnostic is the travel distance until the amount of water in the water reservoir is equal to $l_d$, $\delta$ is the diesel fuel water content, MPG is a number of miles the vehicle may travel per gallon of fuel. A unit conversion factor may be added to equation 5 so that desired units may be provided.

Method 400 also estimates when the amount of water stored in the water reservoir will reach a threshold diagnostic level according to the following equation:

$$days\ to\ diagnostic\ level = \frac{distance\ to\ diagnostic}{\gamma} \qquad (6)$$

where days to diagnostic level is an estimate of a number of days before water in the water reservoir reaches a diagnostic level, distance to diagnostic is a distance the vehicle is expected to travel before water in the water reservoir reaches the diagnostic level, and where $\gamma$ is the distance driven per day is the average distance the vehicle is driven each day. Method 400 proceeds to 414.

At 414, method 400 saves the value of $\delta$ to controller non-volatile memory. Method 400 may also notify the vehicle owner/operator via a human/machine interface of the current water level in the water reservoir ($l_p$), diesel fuel water content δ, distance to diagnostic level, and days to diagnostic level. Method 400 proceeds to 416.

At 416, method 400 judges if a vehicle shutdown is requested. A vehicle shutdown may be requested via input to a human/machine interface or based on vehicle operating conditions. If method 400 judges that a vehicle shutdown has been requested, the answer is yes and method 400 proceeds to exit. Otherwise, the answer is no and method 400 returns to 410.

At 412, method 400 judges if a lower boundary of water in the water reservoir is greater than the minimum water level that may be detected by the water in fuel sensor (e.g., 208 of FIG. 2). Method 400 may estimate the amount of water that is in the water reservoir after a refill of the fuel tank via the following equations:

$$\{f(h_n - h_0) \cdot w_l\}_i < \{water\ added\}_i < \{f(h_n - h_0) \cdot w_h\}_i \quad (7)$$

where f is a function that returns an amount of fuel given arguments $h_n$ and $h_0$, $h_n$ is a fuel level after a fuel fill, $h_0$ is a fuel level before the most recent fuel fill, water added is an amount of water that is added to the fuel tank due to the fuel refill, $w_l$ is the lower boundary of water content in the fuel, $w_h$ is the upper boundary of water content in the fuel, i is a fuel refill event number, and $h_n$ and $h_0$ are as previously described. A lower boundary and an upper boundary of water in the water reservoir may be determined via the following equations:

$$lower\ boundary = \Sigma_i \{f(h_n - h_0) \cdot w_l\}_i \quad (8)$$

$$upper\ boundary = \Sigma_i \{f(h_n - h_0) \cdot w_h\}_i \quad (9)$$

where lower boundary is a lower boundary water level in the water reservoir amount, upper boundary is an upper boundary water level in the water reservoir, and where the other variables are as previously mentioned. If method 400 judges that the lower boundary value is greater than the minimum detectable level of water in fuel ($l_p$), the answer is yes and method 400 proceeds to 413. Otherwise, the answer is no and method 400 proceeds to 416.

At 413, method 400 determines the diesel fuel water content by reading the value of δ from controller non-volatile memory. Method 400 also updates the amount of water in the water reservoir according to the following equation:

$$water_{reservoir} = total\ fuel\ filled \cdot \delta \quad (10)$$

where the variables are as previously mentioned. Method 400 also estimates a number of miles before the water in the water reservoir reaches a diagnostic level as previously described by equation 5. Method 400 also estimates when the amount of water stored in the water reservoir will reach a threshold diagnostic level as previously described by equation 6. Method 400 proceeds to 414.

At 420, method 400 judges if an amount of time between when the low pressure fuel pump is activated and when pressure downstream of the low pressure fuel pump reaches a pressure is greater than a threshold amount of time. The threshold amount of time may be indicative of water being in the fuel after a fuel refill. The inventors herein have determined that pressure downstream of the lower pressure fuel pump increases faster when there is no or less water in the fuel as compared to if there is more water in the fuel. Thus, if the amount of time between when the low pressure fuel pump is activated and a time when pressure downstream of the low pressure fuel pump is less than a threshold amount of time, method 400 judges that less than a threshold amount of water is present in the fuel. If method 400 judges that the amount of time between when the low pressure fuel pump is activated and when pressure downstream of the low pressure fuel pump reaches a pressure is greater than a threshold amount of time, the answer is yes and method 400 proceeds to 430. Otherwise, if method 400 judges that the amount of time between when the low pressure fuel pump is activated and when the pressure downstream of the low pressure fuel pump is less than the threshold amount of time, the answer is no and method 400 proceeds to 422. The threshold amount of time $t_s$ may conform to the following equation:

$$t_s > t_n + 3 \cdot \sigma_n \quad (11)$$

where $t_s$ is the accumulated amount of time for pressure downstream of the low pressure fuel pump to reach a threshold level, $t_n$ is an expected amount of time for pressure downstream of the low pressure pump to build up to a desired pressure, and where $\sigma_n$ is the standard deviation of the amount of time for pressure downstream of the low pressure pump to reach the desired pressure level.

At 422, method 400 revises a standard deviation of the amount of time it takes to observe a predetermined pressure downstream of a low pressure fuel pump after activating the low pressure fuel pump. The mean and standard deviation may be updated according to the following equations:

$$t_{n+1} = \frac{N}{N+1}\left[t_n + \frac{t_b}{N}\right] \quad (12)$$

$$\sigma_{n+1} = \sqrt{\sigma_n^2 + \frac{\left(t_b - \frac{N}{N+1} \cdot \left[t_n + \frac{t_b}{N}\right]\right)^2}{N-1} \cdot \left(\frac{N-1}{N}\right)} \quad (13)$$

were $\sigma_{n+1}$ is the revised standard deviation, $\sigma_n$ is the standard deviation before the revision, $t_b$ is the time between when the low pressure fuel pump is activated and the time when the pressure downstream of the low pressure pump reaches a desired pressure, N is a number of pressure samples, and $t_n$ is the expected amount of time for pressure downstream of the fuel pump to reach the desired pressure.

Method 400 also may estimate the amount of water that is in the water reservoir after a refill of the fuel tank via equation 7 as previously mentioned. Method 400 may also determine the lower boundary and the upper boundary of water in the water reservoir as previously mentioned. In addition, method 400 may determine the total fuel filled according to equation 4. Method 400 proceeds to 410.

At 430, method 400 judges if the diesel exhaust fluid (DEF) reservoir has been refilled. In one example, method 400 may judge that the DEF reservoir has been refilled according to the following equation:

$$h'_n > h'_0 + \varepsilon' \quad (14)$$

where $h'_n$ is the present level output via a DEF level sensor, $h'_0$ is a saved DEF level from a most recent time that the vehicle was deactivated, and $\varepsilon'$ is a threshold offset value for DEF. If method 400 judges that fluid has been added to the DEF reservoir, the answer is yes and method 400 proceeds to 432. Otherwise, the answer is no and method 400 proceeds to 434.

At 432, method 400 judges that DEF may be present in the vehicle's fuel tank and in diesel fuel within the fuel tank. DEF may enter the vehicle's diesel fuel by an operator unintentionally introducing DEF to the diesel fuel tank. Method 400 proceeds to 436.

It should be noted that if method 500 reaches step 430, the pressure downstream of the low pressure fuel pump is indicating a presence of water in fuel. Step 430 may infer that water in the fuel may be due to unintentional addition of DEF to the fuel tank. In particular, method 400 may determine that DEF may have been added to the fuel tank based on the indication of water in fuel (e.g., pressure downstream of low pressure fuel pump) and DEF being added to the DEF reservoir near the time water was detected in the fuel.

At 436, method 400 indicates to a vehicle driver or to a vehicle monitor that water or DEF may be mixed with diesel fuel in the vehicle's fuel tank. Method 400 may display a message to a human/machine interface. Alternatively, or in addition, method 400 may notify a remote server or controller that water or DEF has mixed with diesel fuel so that the vehicle may be serviced. Method 400 proceeds to exit after notifying the vehicle's human driver or a controller or server.

At 434, method 400 concludes that water may be present in the vehicle's diesel fuel. Water may enter the vehicle's diesel fuel by way of condensation within the vehicle's fuel tank or by being pumped with the fuel from a filling station into the vehicle. Method 400 proceeds to 436.

In this way, water or DEF that is mixed with diesel fuel may be identified within a vehicle fuel system. Further, water levels within a water reservoir may be inferred from an estimate of diesel fuel water content so that a vehicle may be serviced before water in the water reservoir reaches a diagnostic level.

The method of FIG. 4 provides for a method for operating a vehicle, comprising: activating a fuel pump and determining an amount of time for a pressure downstream of the fuel pump to reach a threshold pressure in response to an indication of a fuel tank receiving a fluid. The method further comprises indicating water or diesel exhaust fluid is mixed with diesel fuel in response to the amount of time being greater than a threshold amount of time. The method includes where water is indicated to be mixed with the diesel fuel when there is no indication of a diesel exhaust fluid level increasing. The method includes where diesel emission fluid is indicated to be mixed with diesel fuel when there is an indication of a diesel exhaust fluid level increasing. The method includes where the fuel pump supplies diesel fuel to a second fuel pump. The method includes where the amount of time begins when the fuel pump is activated and ends when the pressure downstream of the fuel pump reaches the threshold pressure. The method further comprises estimating a level of water in a water reservoir in response to the amount of time being less than a threshold amount of time.

The method of FIG. 4 also provides for a method for operating a vehicle, comprising: adjusting an estimated reservoir water level to a minimum water level detectable via a water in fuel sensor in response to a water duty cycle being greater than a threshold. The method further comprises adjusting the reservoir water level to a level based on diesel fuel water content and a total fuel fill amount. The method further comprises indicating the reservoir water level via a human/machine interface. The method further comprises indicating water in fuel in response to a pressure downstream of a fuel pump. The method further comprises indicating diesel exhaust fluid in fuel in response to a pressure downstream of a fuel pump.

As will be appreciated by one of ordinary skill in the art, the method described herein may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the objects, features, and advantages described herein, but is provided for ease of illustration and description. Although not explicitly illustrated, one of ordinary skill in the art will recognize that one or more of the illustrated steps, methods, or functions may be repeatedly performed depending on the particular strategy being used.

This concludes the description. The reading of it by those skilled in the art would bring to mind many alterations and modifications without departing from the spirit and the scope of the description. For example, single cylinder, I2, I3, I4, I5, V6, V8, V10, V12 and V16 engines operating in natural gas, gasoline, diesel, or alternative fuel configurations could use the present description to advantage.

The invention claimed is:

1. A method for operating a vehicle, comprising:
activating a first fuel pump and determining an amount of time for a pressure downstream of the first fuel pump to reach a threshold pressure in response to an indication of a fuel tank receiving a fluid, wherein the vehicle comprises the first fuel pump and a second fuel pump, the second fuel pump supplying fuel to an engine.

2. The method of claim 1, further comprising indicating water or diesel exhaust fluid is mixed with diesel fuel in response to the amount of time being greater than a threshold amount of time.

3. The method of claim 2, where water is indicated to be mixed with the diesel fuel when there is no indication of a diesel exhaust fluid level increasing.

4. The method of claim 2, where diesel emission fluid is indicated to be mixed with diesel fuel when there is an indication of a diesel exhaust fluid level increasing.

5. The method of claim 1, where the first fuel pump supplies diesel fuel to the second fuel pump.

6. The method of claim 1, where the amount of time begins when the first fuel pump is activated and ends when the pressure downstream of the first fuel pump reaches the threshold pressure.

7. The method of claim 1, further comprising estimating a level of water in a water reservoir in response to the amount of time being less than a threshold amount of time.

8. A vehicle system, comprising:
an internal combustion engine;
a first fuel pump and a second fuel pump supplying fuel to the internal combustion engine;
a fuel tank; and
a controller including executable instructions stored in non-transitory memory to activate the first fuel pump and determine an amount of time for a pressure downstream of the first fuel pump to reach a threshold pressure in response to an indication of a fluid being added to the fuel tank.

9. The vehicle system of claim 8, further comprising additional instructions to estimate an amount of water in a water reservoir in response to the amount of time being less than a threshold amount of time.

10. The vehicle system of claim 8, further comprising additional instructions to indicate water in a fuel when the amount of time exceeds a threshold amount of time.

11. The vehicle system of claim 8, further comprising additional instructions to indicate diesel exhaust fluid in a fuel when the amount of time exceeds a threshold amount of time.

12. The vehicle system of claim 8, further comprising additional instructions to determine a duty cycle of water stored in a water reservoir.

13. The vehicle system of claim 12, further comprising additional instructions to estimate a diesel fuel water content.

14. The vehicle system of claim 13, further comprising additional instructions to estimate a distance a vehicle may travel before an amount of water stored in a water reservoir reaches a diagnostic level.

15. The vehicle system of claim 13, further comprising additional instructions to adjust a reservoir water level based on a diesel fuel water content.

16. A method for operating a vehicle, comprising:
   activating a first fuel pump and determining an amount of time for a pressure downstream of the first fuel pump to reach a threshold pressure in response to an indication of a fuel tank receiving a fluid;
   supplying fuel to an engine of the vehicle with a second fuel pump; and
   adjusting an estimated reservoir water level to a minimum water level detectable via a water in fuel sensor in response to a water duty cycle being greater than a threshold.

17. The method claim 16, further comprising adjusting the estimated reservoir water level to a level based on diesel fuel water content and a total fuel fill amount.

18. The method of claim 16, further comprising indicating the estimated reservoir water level via a human/machine interface.

19. The method of claim 16, further comprising indicating water in fuel in response to a pressure downstream of the first fuel pump.

20. The method of claim 16, further comprising indicating diesel exhaust fluid in fuel in response to a pressure downstream of the first fuel pump.

* * * * *